United States Patent
Park et al.

(10) Patent No.: US 11,604,130 B2
(45) Date of Patent: Mar. 14, 2023

(54) CABIN AIR STATE SENSING SYSTEM FOR A VEHICLE AND OPERATION METHOD THEREOF

(71) Applicants: Hyundai Motor Company, Seoul (KR); Kia Motors Corporation, Seoul (KR)

(72) Inventors: Ji Min Park, Suwon-si (KR); Yong Chul Kim, Hwaseong-si (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 228 days.

(21) Appl. No.: 17/116,385

(22) Filed: Dec. 9, 2020

(65) Prior Publication Data

US 2021/0372912 A1 Dec. 2, 2021

(30) Foreign Application Priority Data

May 29, 2020 (KR) .................. 10-2020-0065073

(51) Int. Cl.
| | | |
|---|---|---|
| *G01N 15/06* | (2006.01) | |
| *G01N 1/24* | (2006.01) | |
| *B60H 1/00* | (2006.01) | |
| *G01N 33/00* | (2006.01) | |
| *G01K 13/024* | (2021.01) | |

(52) U.S. Cl.
CPC .............. *G01N 15/06* (2013.01); *B60H 1/008* (2013.01); *G01K 13/024* (2021.01); *G01N 1/24* (2013.01); *G01N 33/0036* (2013.01)

(58) Field of Classification Search
CPC .. B60H 1/00792; B60H 1/008; G01K 13/024; G01K 2201/00; G01N 1/2273; G01N 1/24; G01N 15/06; G01N 2015/0046; G01N 33/0036
See application file for complete search history.

(56) References Cited

U.S. PATENT DOCUMENTS

| | | | |
|---|---|---|---|
| 2005/0165527 A1* | 7/2005 | Gorman ............ | B60H 1/00828 701/1 |
| 2017/0158020 A1* | 6/2017 | Park ...................... | G01N 15/06 |
| 2017/0276592 A1* | 9/2017 | Kwon ................. | G01N 15/1429 |
| 2018/0195946 A1* | 7/2018 | Kwon .................... | G01N 21/53 |
| 2019/0283525 A1* | 9/2019 | Dhake .................... | G06V 20/59 |
| 2020/0282796 A1* | 9/2020 | Trapp ................... | B60H 1/0065 |

FOREIGN PATENT DOCUMENTS

| | | | | |
|---|---|---|---|---|
| JP | 2018-008583 A | | 1/2018 | |
| JP | 2018008583 A | * | 1/2018 | ............... B60H 1/00 |
| KR | 20060106983 A | * | 10/2006 | |
| KR | 20100086369 A | * | 7/2010 | |
| KR | 10-2015-0096845 A | | 8/2015 | |

* cited by examiner

*Primary Examiner* — John Fitzgerald
*Assistant Examiner* — Gedeon M Kidanu
(74) *Attorney, Agent, or Firm* — Morgan, Lewis & Bockius LLP

(57) ABSTRACT

A cabin air state sensing system for a vehicle may include a divergence structure facilitating measurement of cabin air temperature and dust concentration in a cabin through suction of air using an air suction device and an operation method thereof.

10 Claims, 11 Drawing Sheets

CABIN AIR STATE SENSING SYSTEM FOR A VEHICLE AND OPERATION METHOD THEREOF

CROSS-REFERENCE TO RELATED APPLICATION

The application claims priority to Korean Patent Application No. 10-2020-0065073, filed May 29, 2020, which is hereby incorporated by reference in its entirety for all purposes.

BACKGROUND OF THE INVENTION

Field of the Invention

The present invention relates to a cabin air state sensing system for a vehicle and an operation method thereof, and, more particularly, to a cabin air state sensing system for a vehicle including a divergence structure facilitating measurement of cabin air temperature and dust concentration in a cabin through suction of air using a single air suction device and an operation method thereof.

Description of Related Art

As fine dust has come to the fore as a serious problem in recent years, a number of related products configured for detecting fine dust concentration and performing air purification to improve, air quality in an indoor space have been provided. Not only buildings, such as houses and offices, these products have been applied also to vehicles where people spend much time.

As shown in FIG. 1, for a vehicle having a function of detecting concentration of fine dust in a cabin or outside the vehicle, a fine dust measurement sensor unit 2 is provided in a Heating, Ventilating, and Air Conditioning (HVAC) system of the vehicle. A motor 12 configured to draw cabin air is provided in the sensor unit 2. When the motor 12 is driven, the cabin air is drawn into the sensor unit 2 through a cabin air introduction portion 4 formed in the cabin. The drawn air is supplied to a sensing portion 22 of the sensor unit 2, whereby fine dust concentration of the drawn in air is measured.

Conventionally, the motor 12 is needed in the fine dust measurement sensor unit 2 to draw a certain amount of cabin air when the dust concentration is measured, which complicates the internal structure of the HVAC system, causes an increase in additional material cost, and increase weight of the HVAC system.

The foregoing is intended merely to aid in the understanding of the background of the present invention, and is not intended to mean that the present invention falls within the purview of the related which is already known to those skilled in the art.

The information included in this Background of the Invention section is only for enhancement of understanding of the general background of the invention and may not be taken as an acknowledgement or any form of suggestion that this information forms the prior art already known to a person skilled in the art.

BRIEF SUMMARY

Various aspects of the present invention are directed to providing cabin air state sensing system for a vehicle, configured for further simplifying a structure for detecting fine dust in vehicles.

Various aspects of the present invention are directed to providing cabin air state sensing system for a vehicle that obviates a separate motor provided at a fine dust concentration sensor.

It is a further object of the present invention to provide a cabin air state sensing system for a vehicle, configured for reducing costs and weight by simplifying the structure.

The objects of the present invention are not limited to those described above. The objects of the present invention will be clearly understood from the following description and could be implemented by means defined in the claims and a combination thereof.

Various aspects of the present invention are directed to providing cabin air state sensing system for a vehicle, the cabin air state sensing system including an air suction device, a main channel having one side connected to the air suction device and the other side connected to a cabin air introduction portion configured to introduce air from a cabin, a cabin air temperature sensor disposed in the main channel to measure temperature of air flowing into the main channel, and a dust sensor disposed in the main channel to measure dust concentration of the air flowing into the main channel, wherein the main channel includes a divergence structure configured to branch the main channel into at least two parts or a connection structure interconnected to the main channel to satisfy required air flow rate of the cabin air temperature sensor and required air flow rate of the dust sensor.

The divergence structure may include a first channel and a second channel, and the first channel and the second channel are formed by dividing the main channel into at least two channels. The cabin air temperature sensor may be disposed in the first channel, and the dust sensor may be disposed in the second channel.

When the required air flow rate of the cabin air temperature sensor and the required air flow rate of the dust sensor are equal, the connection structure may include a connecting channel configured to interconnect the cabin air temperature sensor and the dust sensor in series. The cabin air temperature sensor may be disposed closer to the air suction device than the dust sensor.

In various exemplary embodiments of the present invention, the divergence structure may include a first junction, a third channel and a fourth channel diverging from the first junction, and a second junction where the third channel and the fourth channel are merged with each other to extend to a fifth channel, the cross-sectional area of the third channel may be smaller than the cross-sectional area of the fourth channel, the cross-sectional area of the fifth channel may be equal to the sum of the cross-sectional area of the third channel and the cross-sectional area of the fourth channel, and when the required air flow rate of the cabin air temperature sensor is less than the required air flow rate of the dust sensor, the cabin air temperature sensor may be disposed in the fourth channel and the dust sensor may be disposed in the fifth channel.

In another exemplary embodiment of the present invention, the divergence structure may include a first junction, a third channel and a fourth channel diverging from the first junction, and a second junction where the third channel and the fourth channel are merged with each other to extend to a fifth channel, the cross-sectional area of the third channel may be smaller than the cross-sectional area of the fourth channel, the cross-sectional area of the fifth channel may be equal to the sum of the cross-sectional area of the third channel and the cross-sectional area of the fourth channel, and when the required air flow rate of the cabin air temperature sensor is greater than the required air flow rate of the dust sensor, the dust sensor may be disposed in the fourth channel and the cabin air temperature sensor may be disposed in the fifth channel.

The air suction device may be a motor.

The air suction device may be an aspirator provided in a heating, ventilating, and air conditioning (HVAC) system of a vehicle.

Various aspects of the present invention are directed to providing an operation method of a cabin air state sensing system for a vehicle, the operation method including receiving a request for measuring dust concentration in a cabin, determining a power input state of a blower motor of a vehicle, powering the blower motor on if the blower motor is powered off, and measuring dust concentration through a dust sensor and providing the measured dust concentration.

The operation method may further include determining an air flow rate level of the blower motor after the step of powering the blower motor on, if the air flow rate level of the blower motor is not set to a first level, setting the air flow rate level to the first level, and measuring the dust concentration by the dust sensor and providing the measured dust concentration.

The operation method may further include determining a cabin air discharge mode of the vehicle after the step of setting the air flow rate level of the blower motor to the first step, if the cabin air discharge mode is not a floor mode, setting the cabin air discharge mode to the floor mode, and measuring the dust concentration by the dust sensor and providing the measured dust concentration.

The operation method may further include receiving an off request for the blower motor and stopping measurement of dust concentration.

In various exemplary embodiments of the present invention, the operation method may further include receiving a request for stopping measurement of dust concentration after the step of providing the measured dust concentration, retrieving the power input state of the blower motor at the time of receiving the request for measuring dust concentration in the cabin, and maintaining the power input state of the blower motor identically to the power input state of the blower motor at the time of receiving the request for measuring dust concentration in the cabin.

In another exemplary embodiment of the present invention, the operation method may further include receiving a request for stopping measurement of dust concentration after the step of providing the measured dust concentration, retrieving the cabin air discharge mode determined in the step of determining the cabin air discharge mode, and maintaining the cabin air discharge mode identically to the determined cabin air discharge mode.

Various aspects of the present invention are directed to providing an operation method of a cabin air state sensing system for a vehicle, the operation method including determining a correction factor of a measured value of the dust concentration for each of a plurality of operating conditions of a heating, ventilation, and air conditioning (HVAC) conditioning system, acquiring a measured value of the dust concentration in a cabin through a dust sensor, detecting a current operating condition for the HVAC system, reflecting a correction factor for the detected current operating condition in the measured value to acquire a corrected value, and providing the corrected value.

The correction factor may be set based on operating conditions of the HVAC system including an air flow rate level of the blower motor, a cabin air discharge mode, and a recirculation mode or a fresh air mode.

The effects of the present invention are not limited to those described above, and other effects not mentioned will be clearly recognized by those skilled in the art from the following description.

Other aspects and exemplary embodiments of the present invention are discussed infra.

It is understood that the term "vehicle" or "vehicular" or other similar term as used herein is inclusive of motor vehicles in general such as passenger vehicles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g., fuels derived from resources other than petroleum). As referred to herein, a hybrid vehicle is a vehicle that has two or more sources of power, for example both gasoline-powered and electric-powered vehicles.

The above and other features of the present invention are discussed infra.

The methods and apparatuses of the present invention have other features and advantages which will be apparent from or are set forth in more detail in the accompanying drawings, which are incorporated herein, and the following Detailed Description, which together serve to explain certain principles of the present invention.

Figure 1:
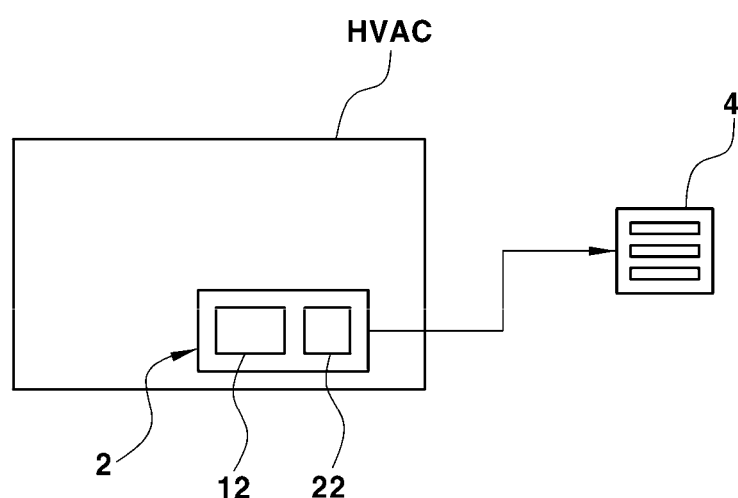
FIG. 1 schematically illustrates a fine dust measurement sensor unit for a vehicle.

It may be understood that the appended drawings are not necessarily to scale, presenting a somewhat simplified representation of various features illustrative of the basic principles of the present invention. The specific design features of the present invention as included herein, including, for example, specific dimensions, orientations, locations, and shapes will be determined in part by the particularly intended application and use environment.

In the figures, reference numbers refer to the same or equivalent portions of the present invention throughout the several figures of the drawing.

DETAILED DESCRIPTION

Reference will now be made in detail to various embodiments of the present invention(s), examples of which are illustrated in the accompanying drawings and described below. While the present invention(s) will be described in conjunction with exemplary embodiments of the present invention it will be understood that the present description is not intended to limit the present invention(s) to those exemplary embodiments. On the other hand, the present invention(s) is/are intended to cover not only the exemplary embodiments of the present invention, but also various alternatives, modifications, equivalents and other embodiments, which may be included within the spirit and scope of the present invention as defined by the appended claims.

It will be understood that, although the terms "first," "second," etc. may be used herein to describe various elements, these elements may not be limited by these terms. These terms are only used to distinguish one element from another element. For instance, a first element discussed below could be termed a second element without departing from the teachings of the present invention. Similarly, the second element could also be termed the first element.

It will be understood that when an element is referred to as being "coupled" or "connected" to another element, it may be directly coupled or connected to the other element or intervening elements may be present therebetween. In contrast, it may be understood that when an element is referred to as being "directly coupled" or "directly connected" to another element, there are no intervening elements present. Other expressions that explain the relationship between elements, such as "between," "directly between," "adjacent to," or "directly adjacent to," may be construed in the same way.

Like reference numerals denote like components throughout the specification. In the meantime, the terminology used herein is for describing various exemplary embodiments only and is not intended to be limiting. As used herein, the singular forms "a," "an," and "the" are intended to include the plural forms as well, unless the context clearly indicates otherwise. It will be further understood that the terms "comprise," "include," "have," etc., when used in the present specification, specify the presence of stated components, steps, operations, and/or elements, but do not preclude the presence or addition of one or more other components, steps, operations, and/or elements thereof.

Hereinafter, the present invention will be described in detail with reference to the accompanying drawings.

A cabin air state sensing system for a vehicle according to various exemplary embodiments of the present invention can measure dust concentration without presence of a motor. That is, the motor provided in the fine dust measurement sensor unit may be obviated, and the sensor unit may be connected to an air suction structure for in-car sensors to draw air, whereby cost and weight of the cabin air state sensing system may be reduced while the structure of the cabin air state sensing system may be further simplified.

A heating, ventilating, and air conditioning (HVAC) system is provided in a vehicle. The HVAC system includes a blower motor, an evaporator, and a heater core to cool, heat, and ventilate the cabin. In addition, the HVAC system includes a cabin air temperature sensor configured to measure temperature in the cabin. The cabin air temperature sensor measures temperature of cabin air drawn through a cabin air introduction portion arranged in a center fascia of the cabin. Air is drawn through the cabin air introduction portion using an aspirator or an active sensor.

The aspirator is provided in the HVAC system and produces negative pressure using movement of air generated by the blower motor of the HVAC system. Due to a pressure difference byte present negative pressure, cabin air is drawn, and the cabin air temperature sensor can measure the temperature of the cabin air.

The active sensor corresponds substantially to a temperature sensor added with a motor and a fan. When the motor in the active sensor is driven, cabin air is forcibly introduced into the active sensor through the cabin air introduction portion, whereby temperature of the cabin air is measured.

The cabin air state sensing system for a vehicle according to various exemplary embodiments of the present invention can be applied to an air suction structure using the aspirator or to the active sensor structure.

In various exemplary embodiments of the present invention, the cabin air state means the state of cabin air observed based on temperature and dust concentration in the cabin and may also include humidity.

Figure 2:
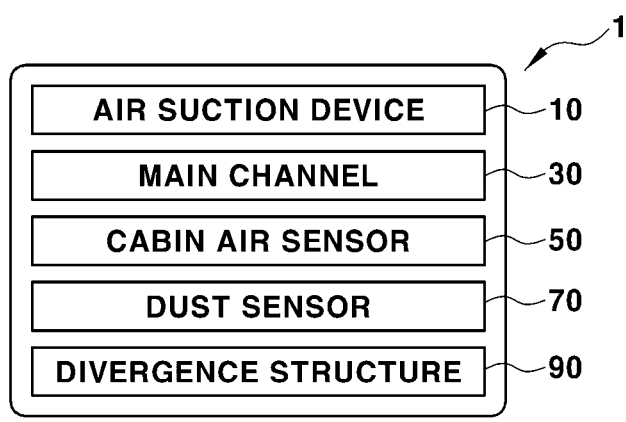
FIG. 2 shows configuration of a cabin air state sensing system for a vehicle according to various exemplary embodiments of the present invention.
Figure 3:
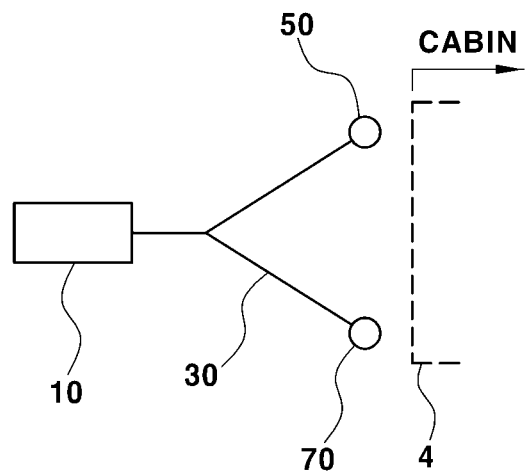
FIG. 3 shows the cabin air state sensing system for a vehicle according to various exemplary embodiments of the present invention.

As shown in FIG. 2 and FIG. 3, the cabin air state sensing system 1 for a vehicle according to various exemplary embodiments of the present invention includes an air suction device 10, a main channel 30, a cabin air temperature sensor 50, and a dust sensor 70, and the main channel 30 includes a divergence structure 90 configured to branch the main channel 30 into two or more parts.

The air suction device 10 may be an aspirator 110 or a motor 210. In case the cabin air temperature sensor 50 is not an active sensor, the air suction device 10 includes an aspirator 110. In case the cabin air temperature sensor 50 is of an active type, the air suction device 10 includes a motor 210. In case the cabin air temperature sensor 50 is an active sensor, a motor mounted in the active sensor can function as the motor 210.

The main channel 30 is connected to the air suction device 10. One side of the main channel 30 is connected to the air suction device 10 in fluid communication, and the other side of the main channel 30 is disposed to fluidically communicate with a cabin air introduction portion 4.

The cabin air temperature sensor 50 is mounted in the main channel 30 and is configured to measure temperature of air flowing in the main channel 30.

In addition, the dust sensor 70 is mounted in the main channel 30. The dust sensor 70 is configured to measure dust concentration of air introduced into the main channel 30 from the cabin. The dust sensor 70 means a sensor configured for measuring concentration of fine dust having small particles in addition to dust having relatively large particles.

In various exemplary embodiments of the present invention, the main channel 30 includes a divergence structure configured to branch the main channel 30 into at least two parts. In the exemplary embodiment, the divergence structure may be interpreted as including a connection structure, as shown in FIG. 5A and FIG. 5B, in addition to a structure in which the main channel 30 is branched into two or more parts, as shown in FIGS. 4A, 4B, and 6A to 7B.

Figure 4A:
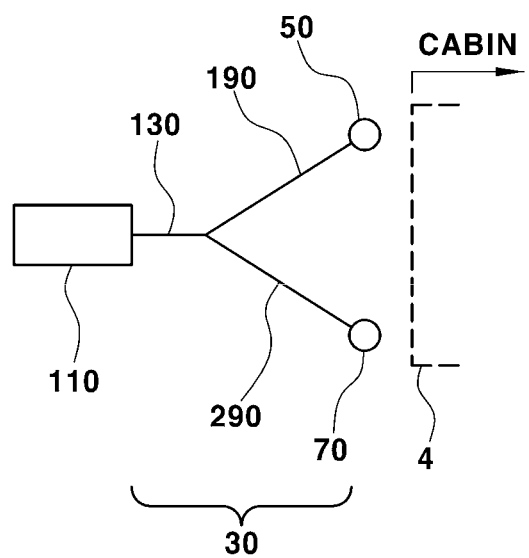
FIG. 4A and FIG. 4B show a cabin air state sensing system for a vehicle according to various exemplary embodiments of the present invention.
Figure 4B:
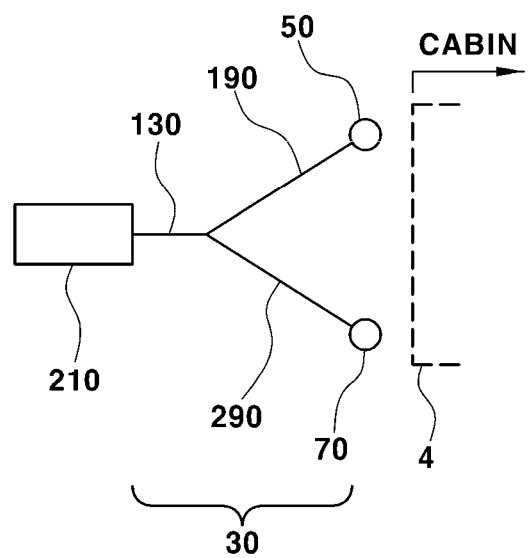
Figure 5A:
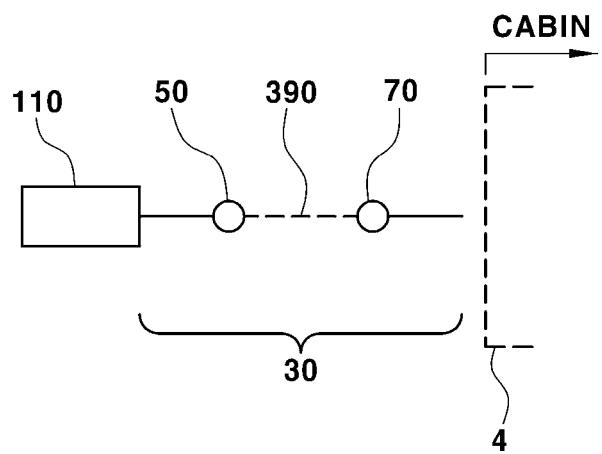
FIG. 5A and FIG. 5B show a cabin air state sensing system for a vehicle according to various exemplary embodiments of the present invention.
Figure 5B:
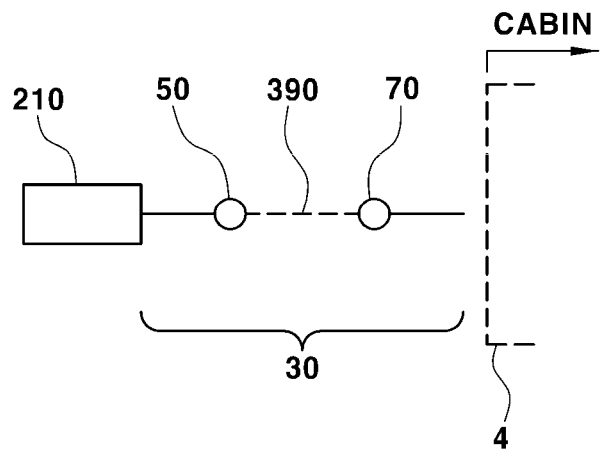
Figure 6A:
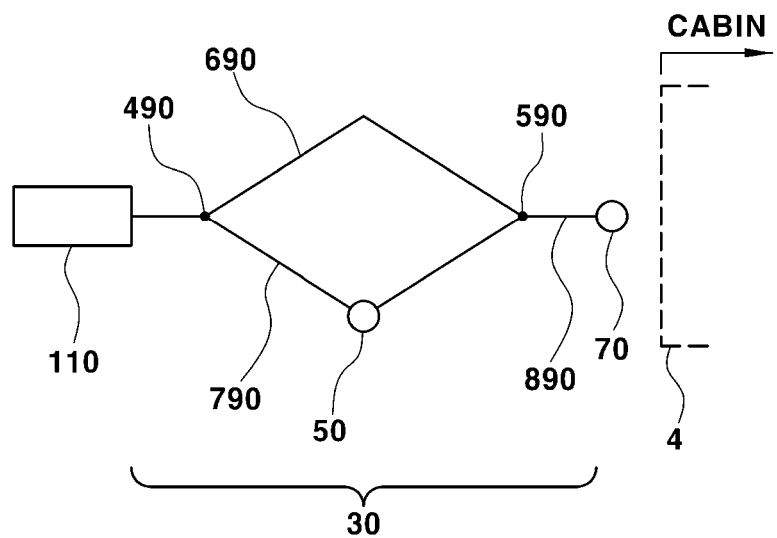
FIG. 6A and FIG. 6B show a cabin air state sensing system for a vehicle according to various exemplary embodiments of the present invention.
Figure 6B:
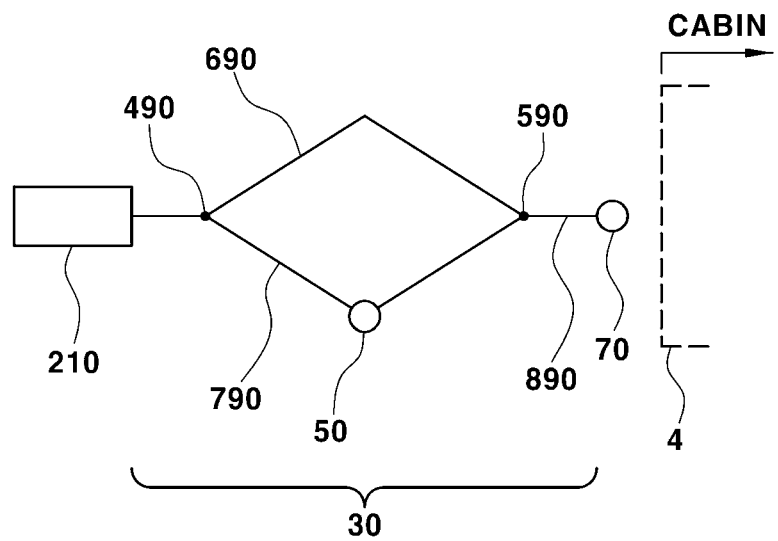

As shown in FIG. 4A and FIG. 4B, according to various exemplary embodiments of the present invention, the divergence structure includes a first channel 190 and a second channel 290 divided from the main channel 30. The main channel 30 includes an extension channel 130 extending from the air suction device 10, and the extension channel 130 may be branched into the first channel 190 and the second channel 290. The air suction device 10 may be the aspirator 110 or the motor 210.

The cabin air temperature sensor 50 is disposed in the first channel 190, and the dust sensor 70 is disposed in the second channel 290. As a result, it is possible to measure both dust concentration and cabin air temperature using one aspirator 110 or one motor 210.

The ratio of cross-sectional areas of the first channel 190 and the second channel 290 may be adjusted based on required air flow rate of the cabin air temperature sensor 50 and the dust sensor 70. According to various exemplary embodiments of the present invention, the ratio of cross-sectional areas of the first channel 190 and the second channel 290 may be varied to satisfy required air flow rate of each sensor under a condition of a sum of the cross-sectional areas of the first channel 190 and the second channel 290 being kept equal to the cross-sectional area of the extension channel 130.

For example, in case a required air flow rate of the cabin air temperature sensor 50 is 2.00 L(liters)/min(minute) and required air flow rate of the dust sensor 70 is 3.68 L/min, the ratio of cross-sectional areas of the first channel 190 where the cabin air temperature sensor 50 is disposed to the second channel 290 where the dust sensor 70 is disposed may be set to about 1:1.8.

According to various exemplary embodiments of the present invention, the main channel 30 may have various divergence structures to meet air flow rate requirement of each of the cabin air temperature sensor 50 and the dust sensor 70.

According to various exemplary embodiments of the present invention, as shown in FIG. 5A and FIG. 5B, in case the required air flow rate of the cabin air temperature sensor 50 and the required air flow rate of the dust sensor 70 are equal to each other, when a type of an aspirator 110 or motor 210 does not allow divergence, the divergence structure may be a connection structure, and the connection structure may include a connecting channel 390 configured to interconnect the cabin air temperature sensor 50 and the dust sensor 70 in series.

The cabin air temperature sensor 50 is disposed closer to the air suction device 10 than the dust sensor 70. Cabin air introduced through the cabin air introduction portion 4 passes through the dust sensor 70, flows along the connecting channel 390, passes through the cabin air temperature sensor 50, and is drawn into the aspirator 110 or the motor 210.

The entirety of the main channel 30 including the connecting channel 390 may have a uniform cross-sectional area.

According to various exemplary embodiments of the present invention, as shown in FIGS. 6A to 7B, in case the required air flow rate of the cabin air temperature sensor 50 and the required air flow rate of the dust sensor 70 are different from each other, the divergence structure includes a first junction 490, a second junction 590, a third channel 690, a fourth channel 790, and a fifth channel 890.

The first junction 490 divides the main channel 30 extending from the aspirator 110 or the motor 210 into two paths. One of the two paths divided by the first junction 490 becomes the third channel 690, and the other the fourth channel 790. The cross-sectional area of the third channel 690 is configured to be smaller than the cross-sectional area of the fourth channel 790. The third channel 690 and the fourth channel 790 separately extend from the first junction 490 and are merged with each other at the second junction 590 to become the fifth channel 890.

According to the various exemplary embodiments of the present invention (see FIG. 6A and FIG. 6B), in case the required air flow rate of the cabin air temperature sensor 50 is less than the required air flow rate of the dust sensor 70, the cabin air temperature sensor 50 is disposed in the fourth channel 790, and the dust sensor 70 is disposed in the fifth channel 890. That is, the fourth channel 790 for the cabin air temperature sensor 50 has a smaller cross-sectional area than the fifth channel 890 for the dust sensor 70. The cross-sectional area of the third channel 690 is adjusted such that the cross-sectional area of the entirety of the main channel 30 is not changed. That is, in the previous example, in case the required air flow rate of the cabin air temperature sensor 50 is 2.00 L/min and required air flow rate of the dust sensor 70 is 3.68 L/min, the ratio of cross-sectional areas or flow rates of the third channel 690, the fourth channel 790, and the fifth channel 890 may be set to 0.8:1.0:1.8.

Figure 7A:
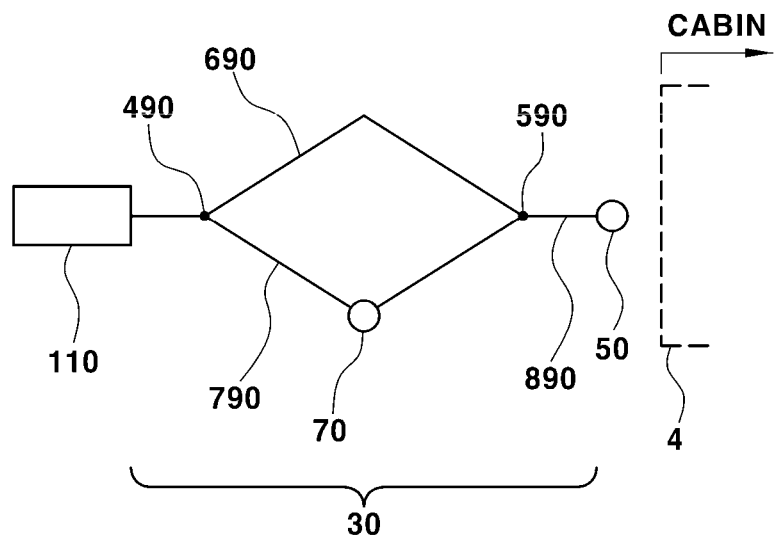
FIG. 7A and FIG. 7B show a cabin air state sensing system for a vehicle according to various exemplary embodiments of the present invention.
Figure 7B:
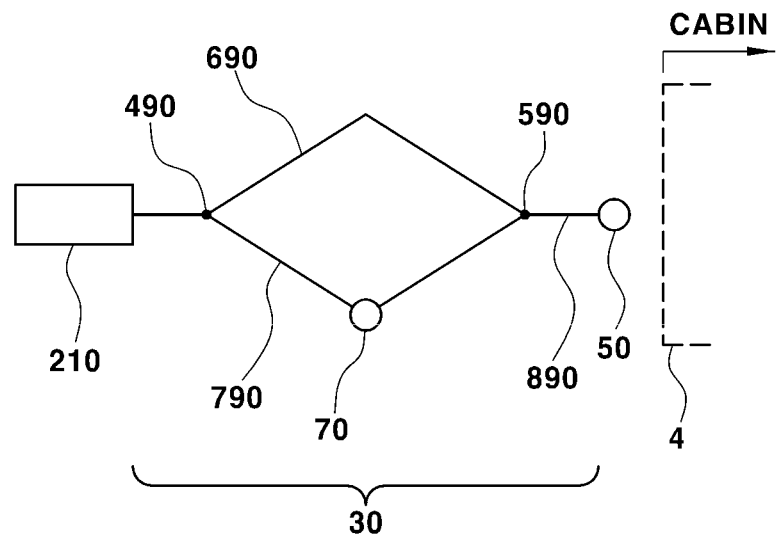

According to the various exemplary embodiments of the present invention (see FIG. 7A and FIG. 7B), in case the required air flow rate of the cabin air temperature sensor 50 is greater than the required air flow rate of the dust sensor 70, the dust sensor 70 is disposed in the fourth channel 790, and the cabin air temperature sensor 50 is disposed in the fifth channel 890. In the same manner as in the various exemplary embodiments of FIGS. 6A and 6B in the present invention, the fourth channel 790 has a smaller cross-sectional area than the fifth channel 890, and the third channel 690 has a smaller cross-sectional area than the fourth channel 790. However, the various exemplary embodiments in FIGS. 7A and 7B is different from the various exemplary embodiments in FIGS. 6A and 6B in that the cabin air temperature sensor 50 having higher required air flow rate is disposed in the fifth channel 890 and the dust sensor 70 is disposed in the fourth channel 790.

Figure 8:
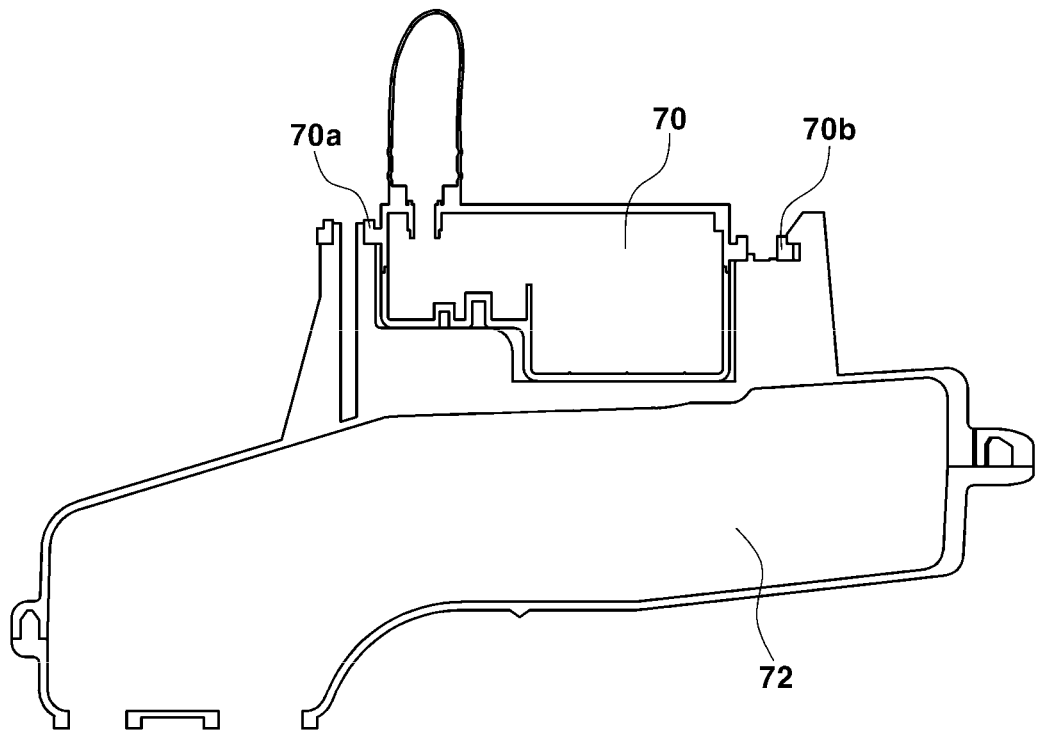
FIG. 8 shows a mounted dust sensor according to various exemplary embodiments of the present invention.

FIG. 8 shows the dust sensor 70 provided at a driver's side shower duct 72. According to various exemplary embodiments of the present invention, the dust sensor 70 may be provided at the driver's side shower duct 72. The shower duct 72 is provided on an upper end portion of the shower duct 72 with a resting surface on which the dust sensor 70 is seated, and one side 70a of the dust sensor 70 is coupled to the shower duct 72 by screw fastening. A hook structure is formed at the other side 70b of the dust sensor 70, and a recess configured for engaging with the hook structure is formed in the shower duct 72, whereby the dust sensor 70 is coupled to the shower duct 72. As a result, the dust sensor 70 can be easily and simply detached after the seat shower duct 72 is separated during maintenance.

Hereinafter, an operation method of the cabin air state sensing system for a vehicle according to various exemplary embodiments of the present invention will be described. Since the operating conditions of the HVAC system affects air suction capability of the aspirator 110, the operation method is applied when the air suction device 10 is the aspirator 110, especially.

Figure 9:
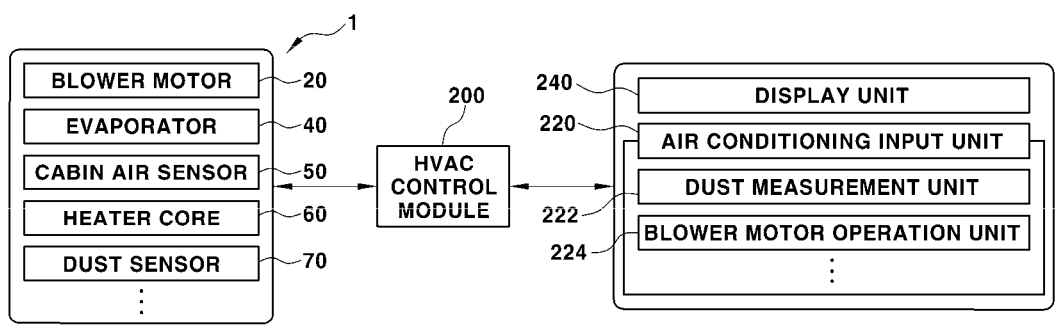
FIG. 9 shows configuration of a heating, ventilating and air conditioning system for a vehicle according to various exemplary embodiments of the present invention.

As shown in FIG. 9, a heating, ventilation, and air conditioning (HVAC) control module 200 configured to control a heating, ventilation, and air conditioning (HVAC) system 100 is provided in a vehicle. The HVAC control module 200 is configured to control respective components of the HVAC system 100. The HVAC control module 200 is configured for communicating with the respective components of the HVAC system 100, such as a blower motor 20, an evaporator 40, a cabin air temperature sensor 50, a heater core 60, and a dust sensor 70, to control the operation of the respective components. Furthermore, the HVAC control module 200 may receive a request from a passenger of the vehicle through an air conditioning input unit 220 disposed on a center fascia in the cabin and operate the HVAC system 100.

Figure 10:
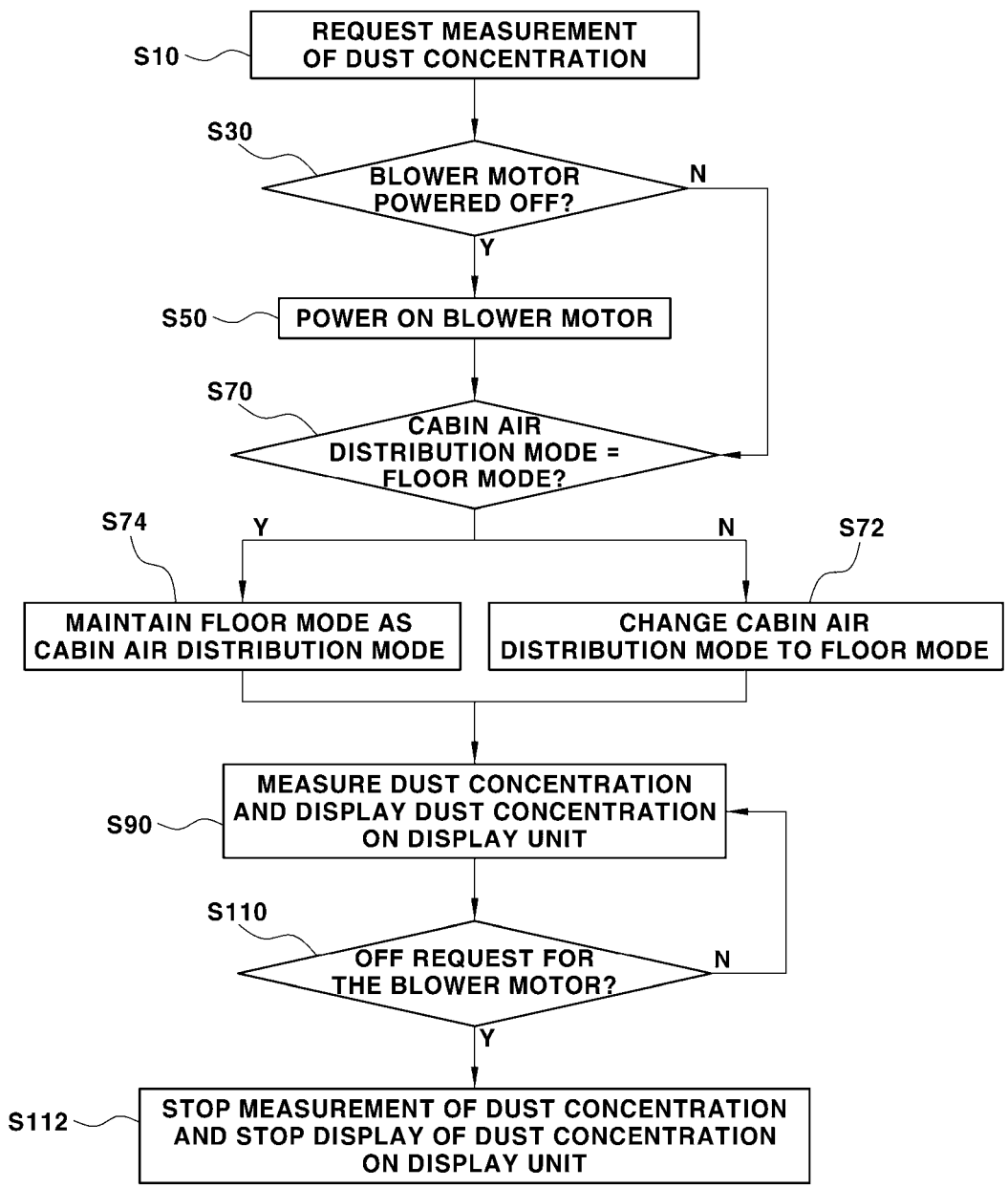
FIG. 10 is a flowchart showing operation of a cabin air state sensing system for a vehicle according to various exemplary embodiments of the present invention.

FIG. 10 shows an operating algorithm of the cabin air state sensing system 1 for a vehicle according to various exemplary embodiments of the present invention.

The HVAC control module 200 receives a request for measuring dust concentration in the cabin (S10). According to various exemplary embodiments of the present invention, the request for measuring dust concentration may be provided by manipulation of a dust measurement unit 222 of the air conditioning input unit 220 in the cabin from a driver or a passenger. Alternatively, measurement of dust concentration may be periodically requested based on settings of the HVAC control module 200.

When the request for measuring dust concentration (S10) is input, the HVAC control module 200 determines the power input state of the blower motor 20 (S30). That is, the HVAC control module 200 determines whether the blower motor 20 is powered on or off.

If blower motor 20 is powered off, the HVAC control module 200 powers the blower motor 20 on (S50).

Figure 11:
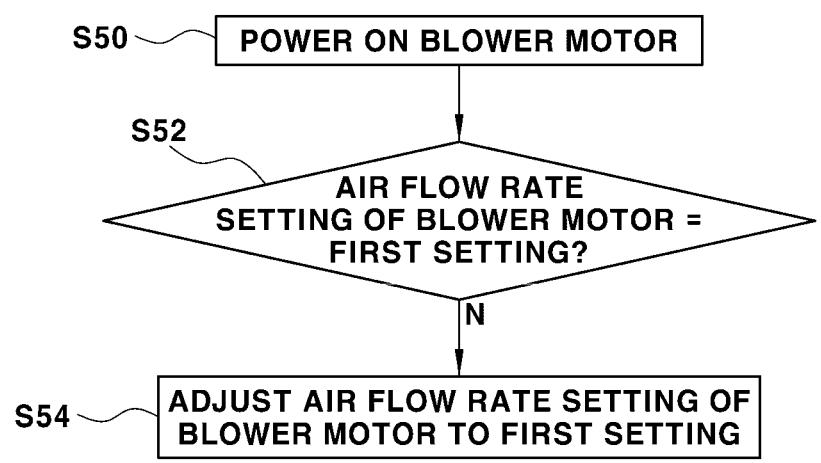
FIG. 11 is a flowchart showing operation of a cabin air state sensing system for a vehicle according to various exemplary embodiments of the present invention.

According to various exemplary embodiments of the present invention, the HVAC control module 200 may set the air flow rate level of the blower motor 20 to a first level, which is the lowest level, at the time of powering on the blower motor 20. According to various exemplary embodiments of the present invention, as shown in FIG. 11, after the blower motor 20 is powered on (S50), the HVAC control module 200 determines the air flow rate level of the blower motor 20 (S52). If the air flow rate level is not set at the first level, which is the lowest step, the HVAC control module 200 adjusts the air flow rate level to the first level (S54). If the air flow rate level is set at the first level, the air flow rate level is maintained.

Furthermore, according to various exemplary embodiments of the present invention, the HVAC control module 200 determines a cabin air discharge mode (S70). The HVAC control module 200 determines whether the current cabin air discharge mode is a face mode, a floor mode, a bi-level mode, a defog mode, or a defrost mode. If the cabin air discharge mode is not set to the floor mode, in which air is discharged toward the feet, the HVAC control module 200 sets the cabin air discharge mode to the floor mode (S72). If the cabin air discharge mode is set to the floor mode, the cabin air discharge mode is maintained (S74).

The HVAC control module 200 commands the dust sensor 70 to measure dust concentration and performs control such that the measured dust concentration is disposed on a display unit 240 in the cabin (S90).

According to various exemplary embodiments of the present invention, upon receiving an off request for the blower motor 20 during measurement of dust concentration (S110), the HVAC control module 200 stops measurement of dust concentration and turns off the display unit 240 (S112). An on or off request for the blower motor 20 may be performed by manipulation of a blower motor operation unit 224 formed at the air conditioning input unit 220. Alternatively, the HVAC control module 200 may receive an off request for the blower motor 20 according to a predetermined time frame.

Figure 12:
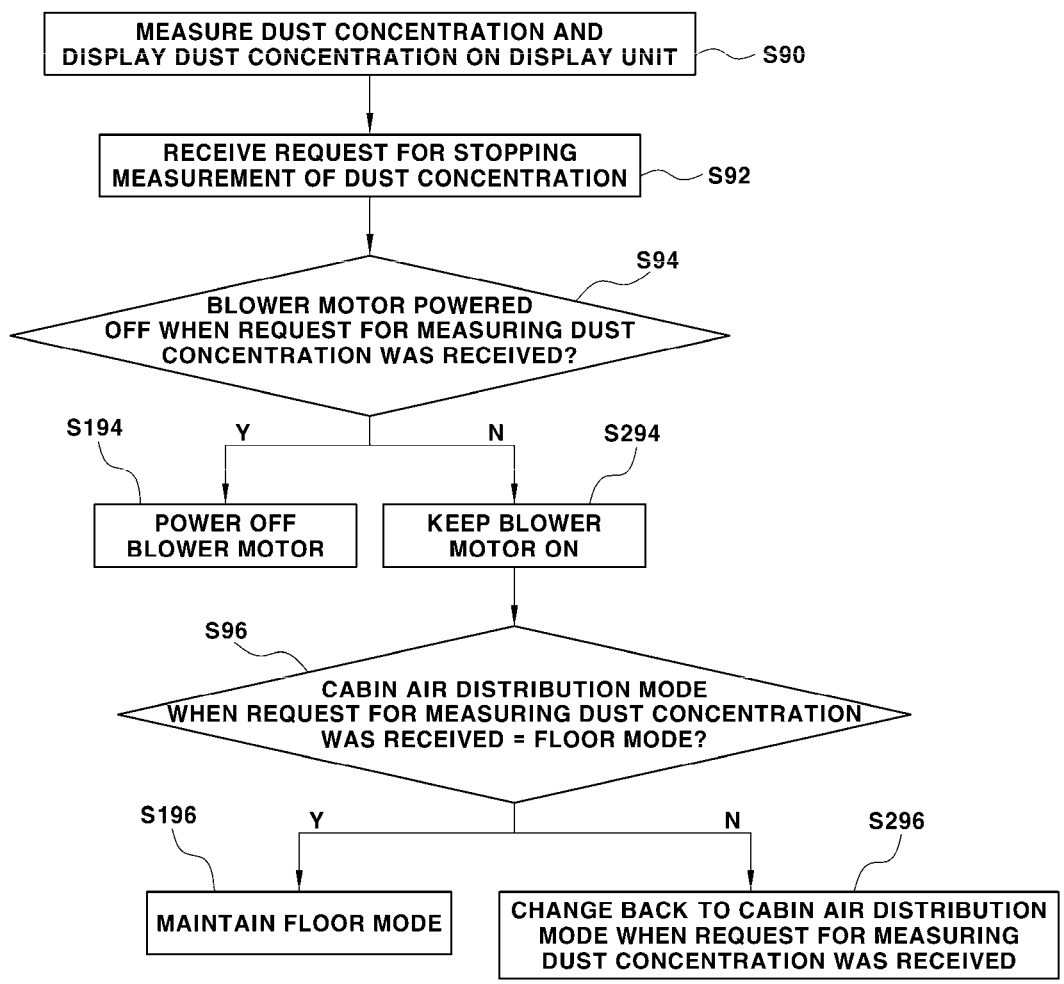
FIG. 12 is a flowchart showing operation of a cabin air state sensing system for a vehicle according to various exemplary embodiments of the present invention.

According to various exemplary embodiments of the present invention, as shown in FIG. 12, for example, upon receiving a request for stopping measurement of dust concentration from a passenger (S92) in the state in which dust concentration which is being measured is displayed on the display unit 240 in the cabin (S90), e.g., during measurement of dust concentration, the HVAC control module 200 determines the power input state of the blower motor 20 when the request for measuring dust concentration was received (S94). If the blower motor 20 was off when the request for measuring dust concentration was received, the HVAC control module 200 powers the blower motor 20 off (S194). On the other hand, if the blower motor 20 was on when the request for measuring dust concentration was received, the HVAC control module 200 keeps the blower motor 20 on (S294).

Furthermore, according to various exemplary embodiments of the present invention, upon receiving a request for stopping measurement of dust concentration in the state in which the measured dust concentration is displayed on the display unit 240 in the cabin (S90), i.e., during measurement of dust concentration, the HVAC control module 200 retrieves the cabin air discharge mode, determined in the cabin air discharge mode determination step (S70), (S96). If the discharge mode determined in the cabin air discharge mode determination step is a floor mode, the discharge mode is maintained (S196). On the other hand, if the determined discharge mode is a mode other than the floor mode, a change to a corresponding mode is performed (S296).

After reception of the request for stopping measurement of dust concentration (S92), determining the power input state of the blower motor 20 (S94) and determining the cabin air discharge mode (S96) may be performed in that order or in reverse order. The HVAC control module 200 is configured to determine the power input state of the blower motor 20 (S94) and then determine the cabin air discharge mode (S96) if the blower motor 20 is on.

According to various exemplary embodiments of the present invention, the HVAC control module 200 corrects the actual value of dust concentration measured by the dust sensor 70 and provides the corrected value of dust concentration. The suction air speed of the aspirator 110 is changed depending on the operating conditions of the HVAC system 100, such as the air flow rate level of the blower motor 20, the cabin air discharge mode, and a cabin air recirculation mode or an external air circulation mode. Since the value of dust concentration measured by the dust sensor 70 is changed by such environmental factors, a factor for each operating condition measured in advance is applied to the actually measured value of dust concentration, whereby it is possible to provide a more accurate corrected value of dust concentration.

Figure 13:
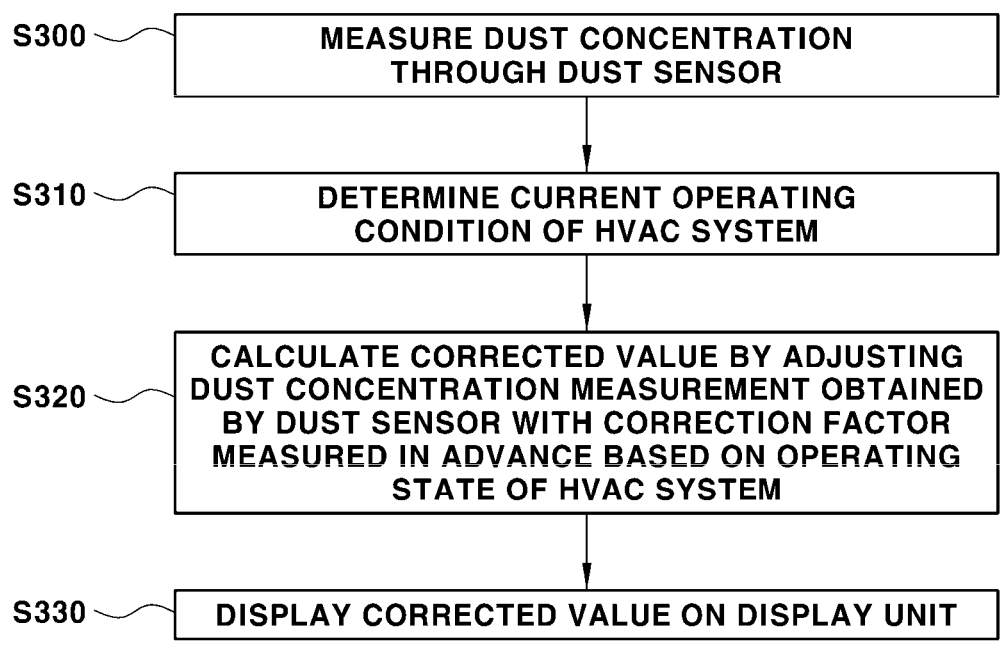
FIG. 13 is a flowchart showing a method of correcting measured dust concentration in a cabin air state sensing system for a vehicle according to various exemplary embodiments of the present invention.

A process of correcting a measured value of the dust concentration will be described with reference to FIG. 13. In response to a request for measuring dust concentration, the dust sensor 70 measures dust concentration in the cabin (S300). At the instant time, the HVAC control module 200 determines the current operating condition of the HVAC system 100 (S310). The HVAC control module 200 determines the air flow rate level of the blower motor 20, the cabin air discharge mode, and whether the cabin air recirculation mode or the external air circulation mode is executed.

Upon receiving the value M measured by the dust sensor 70, the HVAC control module 200 reflects a correction factor F in the measured value to calculate a corrected value C (S320). The correction factor F is determined in advance to more accurately correct the measured value of dust concentration under each operating condition of the air conditioning system (i.e., a combination of conditions, such as the air flow rate level of the blower motor=1, the cabin air discharge mode=FACE, and the external air circulation mode).

According to an example of the present invention, as shown in Table 1, a correction factor F is provided for each air flow rate level of the blower motor 20 and for each cabin air discharge mode, and the measured value M is multiplied by the correction factor F to determine a corrected value C. Correction factors F determined based on the external air circulation mode or the fresh air mode are shown in Table 1. In the case of the cabin air recirculation mode, corrected values C may be determined by multiplying the correction factors F by 1.1.

TABLE 1

| | | Cabin air discharge mode | | | | |
|---|---|---|---|---|---|---|
| | | FACE | BI-LEVEL | FLOOR | MIX | DEFROST |
| Air flow rate level of blower motor | 1 | 4.5 | 6.4 | 5.6 | 9.0 | 7.5 |
| | 2 | 4.3 | 6.1 | 5.4 | 8.6 | 7.2 |
| | 3 | 4.0 | 5.7 | 5.0 | 8.0 | 6.7 |
| | 4 | 3.6 | 5.1 | 4.5 | 7.2 | 6.0 |
| | 5 | 3.1 | 4.4 | 3.9 | 6.2 | 5.2 |
| | 6 | 2.5 | 3.6 | 3.1 | 5.0 | 4.2 |
| | 7 | 1.8 | 2.6 | 2.3 | 3.6 | 3.0 |
| | 8 | 1.0 | 1.4 | 1.3 | 2.0 | 1.7 |

(Based on fresh air mode)

Next, the HVAC control module 200 outputs the corrected value C (S330). That is, the HVAC control module 200 displays the corrected value CH and not the measured value M, on the display unit 240.

As is apparent from the foregoing, according to various exemplary embodiments of the present invention, it is possible to provide a cabin air state sensing system for a vehicle configured for further simplifying a fine dust detecting related structure for vehicles.

Furthermore, according to various exemplary embodiments of the present invention, it is possible to provide a cabin air state sensing system for a vehicle that does not need a separate motor provided at a fine dust concentration sensor, i.e., enables measurement by a cabin air temperature sensor and a dust sensor through suction of air using an air suction device.

According to various exemplary embodiments of the present invention, it is possible to provide a cabin air state sensing system for a vehicle configured for achieving cost reduction and weight reduction by minimizing a related device configured for fine dust concentration measurement.

According to various exemplary embodiments of the present invention, it is possible to provide an operation method of a cabin air state sensing system for a vehicle configured for performing accurate temperature detection and dust concentration measurement.

Furthermore, the term related to a control device such as "controller", "control unit", "control device" or "control module", etc refers to a hardware device including a memory and a processor configured to execute one or more steps interpreted as an algorithm structure. The memory stores algorithm steps, and the processor executes the algorithm steps to perform one or more processes of a method in accordance with various exemplary embodiments of the present invention. The controller according to exemplary embodiments of the present invention may be implemented through a nonvolatile memory configured to store algorithms for controlling operation of various components of a vehicle or data about software commands for executing the algorithms, and a processor configured to perform operation to be described above using the data stored in the memory. The memory and the processor may be individual chips. Alternatively, the memory and the processor may be integrated in a single chip. The processor may be implemented as one or more processors.

The control device may be at least one microprocessor operated by a predetermined program which may include a series of commands for carrying out the method included in the aforementioned various exemplary embodiments of the present invention.

The aforementioned invention can also be embodied as computer readable codes on a computer readable recording medium. The computer readable recording medium is any data storage device that can store data which may be thereafter read by a computer system. Examples of the computer readable recording medium include hard disk drive (HDD), solid state disk (SSD), silicon disk drive (SDD), read-only memory (ROM), random-access memory (RAM), CD-ROMs, magnetic tapes, floppy discs, optical data storage devices, etc and implementation as carrier waves (e.g., transmission over the Internet).

In various exemplary embodiments of the present invention, each operation described above may be performed by a controller, and the controller may be configured by a plurality of controllers, or an integrated single controller.

For convenience in explanation and accurate definition in the appended claims, the terms "upper", "lower", "inner", "outer", "up", "down", "upwards", "downwards", "front", "rear", "back", "inside", "outside", "inwardly", "outwardly", "interior", "exterior", "internal", "external", "inner", "outer", "forwards", and "backwards" are used to describe features of the exemplary embodiments with reference to the positions of such features as displayed in the figures. It will be further understood that the term "connect" or its derivatives refer both to direct and indirect connection.

The foregoing descriptions of specific exemplary embodiments of the present invention have been presented for purposes of illustration and description. They are not intended to be exhaustive or to limit the present invention to the precise forms disclosed, and obviously many modifications and variations are possible in light of the above teachings. The exemplary embodiments were chosen and described to explain certain principles of the present invention and their practical application, to enable others skilled in the art to make and utilize various exemplary embodiments of the present invention, as well as various alternatives and modifications thereof. It is intended that the scope of the present invention be defined by the Claims appended hereto and their equivalents.

What is claimed is:

1. A cabin air state sensing system for a vehicle, the cabin air state sensing system comprising:
   an air suction device;
   a main channel having one side connected to the air suction device and the other side connected to a cabin air introduction portion configured to introduce air from a cabin;

a cabin air temperature sensor disposed in the main channel to measure temperature of air flowing in the main channel; and a dust sensor disposed in the main channel to measure dust concentration of the air flowing in the main channel, wherein the main channel includes a divergence structure of branching the main channel into at least two portions or a connection structure interconnected to the main channel to satisfy required air flow rate of the cabin air temperature sensor and required air flow rate of the dust sensor, wherein the divergence structure includes a first channel and a second channel, and the first channel and the second channel are formed by dividing the main channel into at least two channels, wherein distal ends of the first channel and the second channel are open ends connected to the cabin air introduction portion, and wherein the cabin air temperature sensor is disposed in the first channel, and wherein the dust sensor is disposed in the second channel.

2. The cabin air state sensing system according to claim 1, wherein the air suction device is a motor.

3. The cabin air state sensing system according to claim 1, wherein the air suction device is an aspirator provided in a heating, ventilating, and air conditioning (HVAC) system of the vehicle.

4. A cabin air state sensing system for a vehicle, the cabin air state sensing system comprising:
an air suction device;
a main channel having one side connected to the air suction device and the other side connected to a cabin air introduction portion configured to introduce air from a cabin;
a cabin air temperature sensor disposed in the main channel to measure temperature of air flowing in the main channel; and
a dust sensor disposed in the main channel to measure dust concentration of the air flowing in the main channel,
wherein the main channel includes a divergence structure of branching the main channel into at least two portions or a connection structure interconnected to the main channel to satisfy required air flow rate of the cabin air temperature sensor and required air flow rate of the dust sensor,
wherein the divergence structure of the main channel includes:
a first junction to which the air suction device is connected;
a third channel and a fourth channel diverging from the first junction; and
a second junction where the third channel and the fourth channel are merged with each other to extend to a fifth channel, wherein a cross-sectional area of the third channel is smaller than a cross-sectional area of the fourth channel and a cross-sectional area of the fifth channel is equal to a sum of the cross-sectional area of the third channel and the cross-sectional area of the fourth channel,
wherein when the required air flow rate of the cabin air temperature sensor is less than the required air flow rate of the dust sensor, the cabin air temperature sensor is disposed in the fourth channel and the dust sensor is disposed in the fifth channel.

5. The cabin air state sensing system according to claim 4, wherein when the required air flow rate of the cabin air temperature sensor is greater than the required air flow rate of the dust sensor, the dust sensor is disposed in the fourth channel and the cabin air temperature sensor is disposed in the fifth channel.

6. An operation method of a cabin air state sensing system for a vehicle, the cabin air state sensing system including: an aspirator provided in a heating, ventilating, and air conditioning (HVAC) system of the vehicle; a main channel having one side connected to the aspirator and the other side connected to a cabin air introduction portion configured to introduce air from a cabin; a cabin air temperature sensor disposed in the main channel to measure temperature of air flowing in the main channel; and a dust sensor disposed in the main channel to measure dust concentration of the air flowing in the main channel, wherein the main channel includes a divergence structure of branching the main channel into at least two portions or a connection structure interconnected to the main channel to satisfy required air flow rate of the cabin air temperature sensor and required air flow rate of the dust sensor, the operation method including:
receiving a request for measuring dust concentration in the cabin;
determining a power input state of a blower motor of the vehicle;
powering the blower motor on when the blower motor is powered off;
measuring the dust concentration by the dust sensor and providing the measured dust concentration,
determining an air flow rate level of the blower motor after powering the blower motor on;
when the air flow rate level of the blower motor is not set to a first level, setting the air flow rate level to the first level; and
measuring the dust concentration by the dust sensor and providing the measured dust concentration.

7. The operation method according to claim 6, further including:
receiving an off request for the blower motor; and
stopping the measuring of the dust concentration.

8. The operation method according to claim 6, further including:
receiving a request for stopping the measuring of the dust concentration after providing the measured dust concentration;
retrieving the power input state of the blower motor at a time of receiving the request for measuring the dust concentration in the cabin; and
maintaining the power input state of the blower motor identically to the power input state of the blower motor at the time of receiving the request for measuring the dust concentration in the cabin.

9. The operation method according to claim 6, further including:
determining a cabin air discharge mode of the vehicle after setting the air flow rate level of the blower motor to the first level;
when the cabin air discharge mode is not a floor mode, setting the cabin air discharge mode to the floor mode; and
measuring the dust concentration by the dust sensor and providing the measured dust concentration.

10. The operation method according to claim 9, further including:
receiving a request for stopping the measuring of the dust concentration after providing the measured dust concentration;

retrieving the cabin air discharge mode determined in the determining the cabin air discharge mode; and maintaining the cabin air discharge mode identically to the determined cabin air discharge mode.

* * * * *